US008100820B2

(12) United States Patent
Hauser et al.

(10) Patent No.: US 8,100,820 B2
(45) Date of Patent: Jan. 24, 2012

(54) IMPLANTABLE DEVICE FOR TREATMENT OF VENTRICULAR DILATION

(75) Inventors: David L. Hauser, Newport Beach, CA (US); Jan Otto Solem, Stetten (CH)

(73) Assignee: Edwards Lifesciences Corporation, Irvine, CA (US)

( * ) Notice: Subject to any disclaimer, the term of this patent is extended or adjusted under 35 U.S.C. 154(b) by 1189 days.

(21) Appl. No.: 11/843,628

(22) Filed: Aug. 22, 2007

(65) Prior Publication Data

US 2009/0054724 A1 Feb. 26, 2009

(51) Int. Cl.
 *A61F 2/00* (2006.01)
(52) U.S. Cl. .......................................................... 600/37
(58) Field of Classification Search .............. 600/16–18, 600/37; 623/1.16, 1.2, 1.3, 1.31, 11.11, 23.7; 128/897, 898
See application file for complete search history.

(56) References Cited

U.S. PATENT DOCUMENTS

| | | | |
|---|---|---|---|
| 4,655,771 A | 4/1987 | Wallsten | |
| 5,064,435 A | 11/1991 | Porter | |
| 5,071,407 A | 12/1991 | Termin et al. | |
| 5,170,802 A | 12/1992 | Mehra | |
| 5,209,730 A | 5/1993 | Sullivan | |
| 5,224,491 A | 7/1993 | Mehra | |
| 5,304,131 A | 4/1994 | Paskar | |
| 5,382,259 A | 1/1995 | Phelps et al. | |
| 5,383,892 A | 1/1995 | Cardon et al. | |
| 5,390,661 A | 2/1995 | Griffith et al. | |
| 5,441,515 A | 8/1995 | Khosravi et al. | |
| 5,449,373 A | 9/1995 | Pinchasik et al. | |
| 5,496,275 A | 3/1996 | Sirhan et al. | |
| 5,531,779 A | 7/1996 | Dahl et al. | |
| 5,545,209 A | 8/1996 | Roberts et al. | |
| 5,591,197 A | 1/1997 | Orth et al. | |
| 5,607,444 A | 3/1997 | Lam | |
| 5,713,949 A | 2/1998 | Jayaraman | |
| 5,817,126 A | 10/1998 | Imran | |
| 5,876,433 A | 3/1999 | Lunn | |
| 5,891,108 A | 4/1999 | Leone et al. | |
| 5,935,081 A | 8/1999 | Kadhiresan | |
| 5,954,761 A | 9/1999 | Machek et al. | |
| 5,961,545 A | 10/1999 | Lentz et al. | |
| 5,980,522 A | 11/1999 | Koros et al. | |

(Continued)

FOREIGN PATENT DOCUMENTS

WO        WO 96/34211        10/1996

(Continued)

OTHER PUBLICATIONS

Buchanan, et al., Circumferential Suture of the Mitral Annulus for Correction of Mitral Regurgitation in Dogs, Veterinary Surgery, 27:182-193, 1998.

*Primary Examiner* — Samuel Gilbert
(74) *Attorney, Agent, or Firm* — David L. Hauser

(57) ABSTRACT

A device and method for reducing ventricular dilation by placing one or more cardiac bridges into vessels extending along a length of the ventricle. Each cardiac bridge preferably includes a pair of anchors and a bridge member secured therebetween. The tension in the bridge member is increased to compress the ventricle and thereby reduce the dilation. In another embodiment, the bridge member is tensioned to reshape the left ventricle for reducing tension on the chordae tendinae in the heart to improve valve function.

13 Claims, 12 Drawing Sheets

U.S. PATENT DOCUMENTS

| | | |
|---|---|---|
| 6,006,122 A | 12/1999 | Smits |
| 6,013,854 A | 1/2000 | Moriuchi |
| 6,019,739 A | 2/2000 | Rhee et al. |
| 6,051,020 A | 4/2000 | Goicoechea et al. |
| 6,077,296 A | 6/2000 | Shokoohi et al. |
| 6,093,203 A | 7/2000 | Uflacker |
| 6,110,100 A | 8/2000 | Talpade |
| 6,123,699 A | 9/2000 | Webster, Jr. |
| 6,161,029 A | 12/2000 | Spreigl et al. |
| 6,161,543 A | 12/2000 | Cox et al. |
| 6,165,169 A | 12/2000 | Panescu et al. |
| 6,168,619 B1 | 1/2001 | Dinh et al. |
| 6,171,329 B1 | 1/2001 | Shaw et al. |
| 6,210,432 B1 | 4/2001 | Solem et al. |
| 6,368,348 B1 | 4/2002 | Gabbay |
| 6,402,781 B1 | 6/2002 | Langberg et al. |
| 6,537,314 B2 | 3/2003 | Langberg et al. |
| 6,569,198 B1 | 5/2003 | Wilson et al. |
| 6,629,534 B1 | 10/2003 | Dell et al. |
| 6,656,221 B2 | 12/2003 | Taylor et al. |
| 6,676,702 B2 | 1/2004 | Mathis |
| 6,706,065 B2 | 3/2004 | Langberg et al. |
| 6,709,456 B2 | 3/2004 | Langberg et al. |
| 6,764,510 B2 | 7/2004 | Vidlund et al. |
| 6,790,231 B2 | 9/2004 | Liddicoat et al. |
| 6,800,090 B2 | 10/2004 | Alferness et al. |
| 6,810,882 B2 | 11/2004 | Langberg et al. |
| 6,890,353 B2 | 5/2005 | Cohn et al. |
| 6,908,478 B2 | 6/2005 | Alferness et al. |
| 6,989,028 B2 | 1/2006 | Lashinski et al. |
| 6,997,951 B2 | 2/2006 | Solem et al. |
| 7,011,682 B2 | 3/2006 | Lashinski et al. |
| 7,044,967 B1 | 5/2006 | Solem et al. |
| 7,090,695 B2 * | 8/2006 | Solem et al. ............... 623/2.37 |
| 7,144,363 B2 | 12/2006 | Pai et al. |
| 7,637,946 B2 * | 12/2009 | Solem et al. ............... 623/2.37 |
| 7,717,954 B2 * | 5/2010 | Solem et al. ............... 623/2.36 |
| 2001/0018611 A1 | 8/2001 | Solem et al. |
| 2002/0019660 A1 | 2/2002 | Gianotti et al. |
| 2002/0087173 A1 | 7/2002 | Alferness et al. |
| 2002/0111647 A1 | 8/2002 | Khairkhahan et al. |
| 2002/0183838 A1 | 12/2002 | Liddicoat et al. |
| 2002/0188170 A1 | 12/2002 | Santamore et al. |
| 2003/0078465 A1 | 4/2003 | Pai et al. |
| 2003/0083538 A1 | 5/2003 | Adams et al. |
| 2003/0120341 A1 | 6/2003 | Shennib et al. |
| 2003/0135267 A1 | 7/2003 | Solem et al. |
| 2003/0171806 A1 | 9/2003 | Mathis et al. |
| 2003/0204138 A1 | 10/2003 | Choi |
| 2004/0073302 A1 | 4/2004 | Rourke et al. |
| 2004/0102840 A1 | 5/2004 | Solem et al. |
| 2004/0102841 A1 | 5/2004 | Langberg et al. |
| 2004/0133220 A1 | 7/2004 | Lashinski et al. |
| 2004/0138744 A1 | 7/2004 | Lashinski et al. |
| 2004/0176840 A1 | 9/2004 | Langberg et al. |
| 2004/0254600 A1 | 12/2004 | Zarbatany et al. |
| 2005/0043792 A1 | 2/2005 | Solem et al. |
| 2005/0060030 A1 | 3/2005 | Lashinski et al. |
| 2005/0080483 A1 | 4/2005 | Solem et al. |
| 2005/0096740 A1 | 5/2005 | Langberg et al. |
| 2005/0177228 A1 | 8/2005 | Solem et al. |
| 2005/0222678 A1 | 10/2005 | Lashinski et al. |
| 2006/0116756 A1 | 6/2006 | Solem et al. |
| 2006/0116757 A1 | 6/2006 | Lashinski et al. |
| 2006/0129051 A1 | 6/2006 | Rowe et al. |
| 2006/0184230 A1 | 8/2006 | Solem et al. |
| 2006/0276890 A1 | 12/2006 | Solem et al. |
| 2007/0038297 A1 | 2/2007 | Bobo et al. |
| 2007/0073391 A1 | 3/2007 | Bonrang et al. |
| 2007/0173926 A1 | 7/2007 | Bobo et al. |

FOREIGN PATENT DOCUMENTS

| | | |
|---|---|---|
| WO | WO 98/51365 | 11/1998 |
| WO | WO 99/44534 | 9/1999 |
| WO | WO 00/18320 | 4/2000 |
| WO | WO 01/00111 | 1/2001 |
| WO | WO 01/89426 | 11/2001 |
| WO | WO 02/00099 | 1/2002 |
| WO | WO 02/060352 | 8/2002 |
| WO | WO 02/076284 | 10/2002 |
| WO | WO 02/078576 | 10/2002 |
| WO | WO 03/037171 | 5/2003 |
| WO | WO 03/055417 | 7/2003 |
| WO | WO 2004/019816 | 3/2004 |
| WO | WO 2004/045463 | 6/2004 |

* cited by examiner

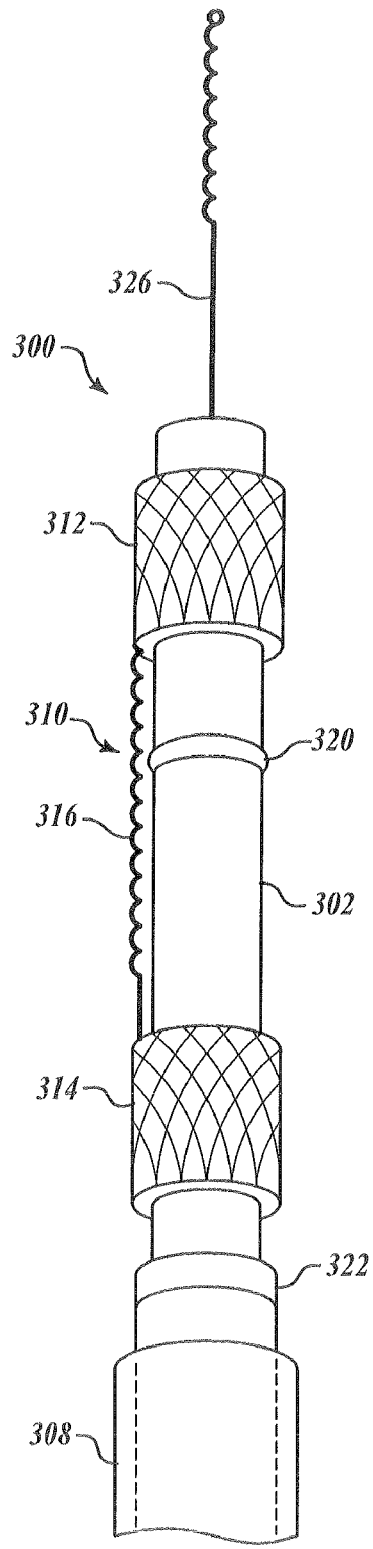
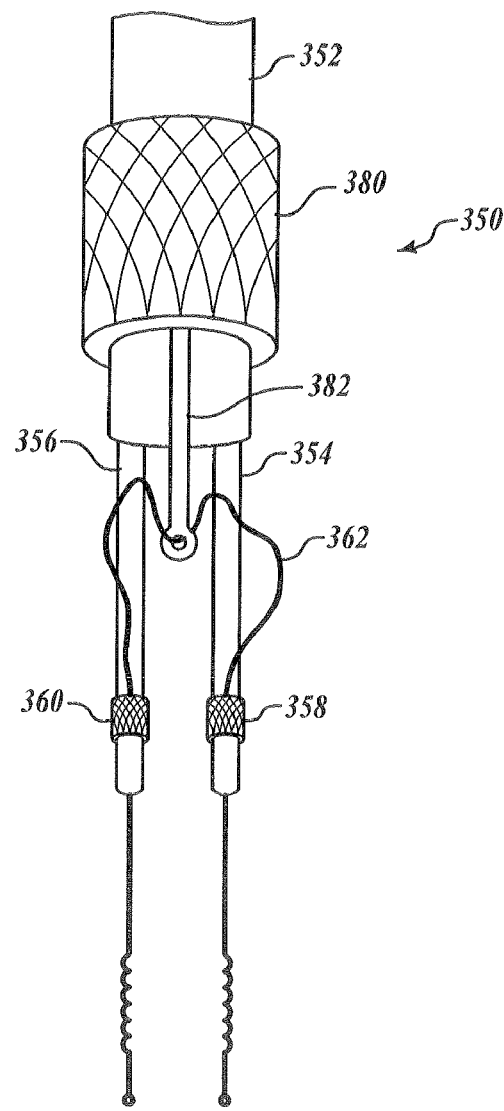
*FIG.11A*   *FIG.11B*

IMPLANTABLE DEVICE FOR TREATMENT OF VENTRICULAR DILATION

FIELD

The following disclosure relates generally to medical devices and methods of use. More particularly, the following disclosure relates to devices and methods for treating ventricular dilation.

BACKGROUND

Ventricular dilation (also referred to as ventricular dilatation) is a condition wherein the wall of the heart muscle thins and/or expands as compared to a healthy heart. For a variety of reasons, a dilated ventricle often exhibits a reduced ability to pump blood. As a result, this condition typically increases the load on the heart while decreasing cardiac efficiency. One reason for the increased load on the heart is that blood is pumped in a direction other than directly towards the heart valve (e.g., aortic valve). Another reason for the increased load on the heart is that the enlarged ventricle can negatively affect the operation of one or more heart valves. More particularly, if the leaflets of a heart valve are not aligned properly due to an enlarged valve annulus, the leaflets may not close tightly. Incomplete leaflet closure leads to regurgitation of blood through the valve.

In recent years, it has been discovered that ventricular dilation is a relatively common condition in elderly people that contributes to fatigue when performing physical activities such as walking. Unfortunately, in many cases, patients having this condition lead very limited lives. Due to the prevalence of this condition, a number of treatments have been proposed for treating ventricular dilation.

Certain proposed treatments utilize external supports, such as sacs or wraps, which are configured to be placed around the exterior of the heart to shore up the ventricular walls in an effort to improve its pumping efficiency. Other treatments involve surgically remodeling the ventricle by removing a portion of the muscular wall. Still other treatments involve pharmacological treatments, such as diuretics, and mechanical pumps for reducing the load on the heart by assisting with the pumping function which is normally performed by the heart. Although many of these treatments have been studied extensively, none of these treatments has met with great success. Furthermore, many of these treatments are highly invasive and may not be appropriate for patients that are already in a weakened cardiac condition. In fact, many believe that the risks of the existing procedures outweigh the potential benefits. As a result, the growing patient population afflicted with this condition is not being adequately treated. Therefore, an urgent need exists for a less invasive and more effective technique for treating ventricular dilation.

SUMMARY

The present disclosure relates to a minimally invasive technique for treating ventricular dilation. In one embodiment, an implantable device is placed within a blood vessel extending along a length of the dilated ventricle. The implantable device includes at least one anchor positioned within the vessel and a bridge member secured to the anchor. A second anchor may be positioned within or outside the vessel. The bridge member is tensioned between the anchors for applying a compressive force along the dilated ventricular wall. The bridge member may include a bioabsorbable material that allows the bridge member to gradually contract over time after it is implanted into the body.

In one embodiment, the implantable bridge takes the form of a cardiac bridge which is placed in a vein along the heart muscle. The cardiac bridge is preferably deployed by advancing a delivery catheter through the inferior or superior vena cava to the right atrium of the heart, through the coronary ostium and into the coronary sinus to allow the vein to be reached. One or more anchors are inserted into the vein and the bridge member is tensioned to reduce the dilation and restore the heart to a more normal shape. In various preferred embodiments, a cardiac bridge may be deployed in the middle cardiac vein, the posterior vein of the left ventricle, or the left marginal vein. In other embodiments, the cardiac bridge may be deployed in the great cardiac vein or the diagonal vein.

In accordance with another aspect of the disclosed technology, a cardiac bridge includes a distal anchor that is placed in a cardiac vessel and a bridge member that extends out of the body when the distal anchor is deployed. A second anchor is advanced over two or more bridge members to secure the two or more bridge members together.

In accordance with yet another aspect of the disclosed technology, a deployment device includes a catheter having a proximal anchor on an outer surface thereof. Within the catheter is a pair of sheaths each having a distal anchor thereon and a cover of the sheaths. The distal anchors are connected together by a bridge member and to the proximal anchor by a tether.

In accordance with yet another embodiment, the disclosed technology is used to improve the operation of valves in the heart. In one preferred configuration, one or more cardiac bridges are configured to reshape the heart for reducing undesirable tension on the chordae tendinae. The chordae tendineae are cord-like tendons that connect the papillary muscles to the mitral valve and the tricuspid valve in the heart. A dilated ventricle can increase the tension in the chordae tendinae, thereby negatively impacting the operation of the mitral or triscupid valve. By reshaping the heart with cardiac bridges, the tension in the chordae tendinae is relieved and the function of the heart valve is improved.

BRIEF DESCRIPTION OF THE DRAWINGS

The foregoing and other objects, features, and advantages of the invention will become more apparent from the following detailed description, which proceeds with reference to the accompanying figures.

FIG. 11A illustrates one embodiment of a delivery device for placing a cardiac bridge in a vessel surrounding the heart;

FIG. 11B illustrates another embodiment of a delivery device for placing a cardiac bridge with two or more anchors into different vessels of the heart;

DETAILED DESCRIPTION

Figure 1:
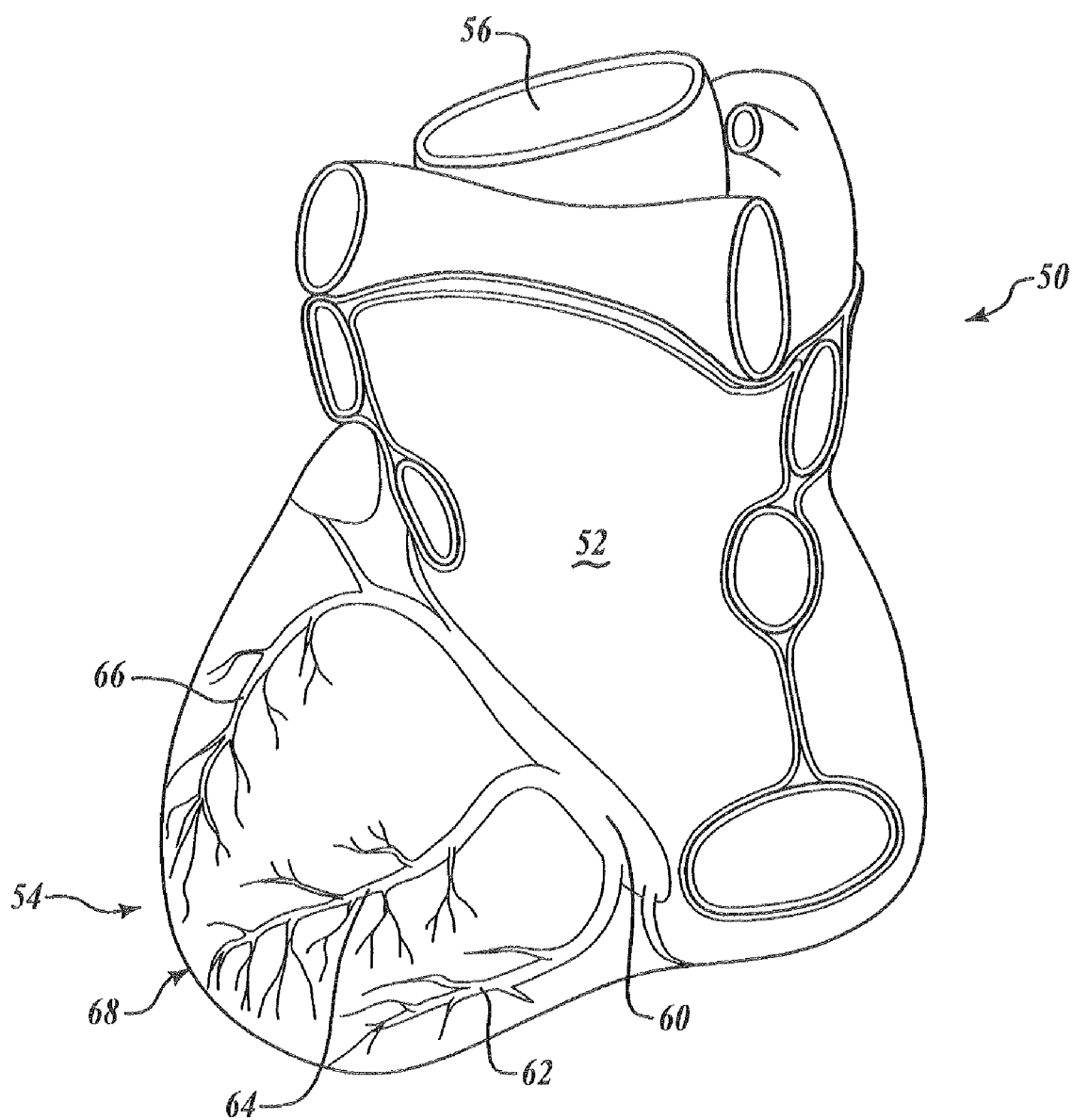
FIG. 1 is a posterior view of a human heart illustrating a number of veins that extend along the left ventricle.

With reference now to FIG. 1, a posterior view of a human heart is provided for purposes of illustration. The heart 50 includes a left atrium 52 that receives oxygenated blood returning from the lungs and supplies it to a left ventricle 54. Upon contraction of the left ventricle 54, the blood is pumped into the aorta 56 where it is delivered throughout the body.

Surrounding the heart ventricle 54 are a number of arteries (not shown) that supply oxygenated blood to the heart muscle and a number of veins that return the blood from the heart muscle to the right atrium. The coronary sinus 60 is a relatively large vein that extends generally around the upper portion of the left ventricle 54 and provides a return conduit for blood returning to the right atrium. The coronary sinus terminates at the coronary ostium (not shown) at which point the blood enters the right atrium. As illustrated, a number of smaller veins deliver blood from the heart muscle to the coronary sinus. These veins include the middle cardiac vein 62, the posterior vein of the left ventricle 64 and the left marginal vein 66. Each of these veins extends generally upward along a length of the left ventricle from a location near the apex 68 of the heart to the coronary sinus 60.

Ventricular dilation occurs when a ventricle of the heart becomes enlarged as compared with a healthy heart muscle. According to one preferred embodiment of the present invention, one or more cardiac bridges are configured to be positioned in veins that extend along the outside of the heart for treating ventricular dilation. As will be explained below, the cardiac bridge is adapted to exert a compressive force on the ventricle, thereby reducing the dilation of the heart wall. Although the following disclosure describes positioning cardiac bridges within veins extending along a length of the left ventricle, it will be appreciated that one or more cardiac bridges could also be placed in vessels extending along a length of the right ventricle of the heart or extending along a length of both the left and right ventricles or other vessels such as the great cardiac vein or the diagonal vein. Furthermore, although the following disclosure describes deploying cardiac bridges within the veins of heart muscle, one or more the cardiac bridges may also be placed in the arteries of the heart without departing from the scope of the invention. However, great care must be taken when deploying the cardiac bridges within arteries of the heart because any restriction of blood flow or possible blockage in an artery is a serious patient complication. Nonetheless, for the purpose of this application, the term "cardiac vessel" is intended to mean either a vein or an artery.

Figure 2:
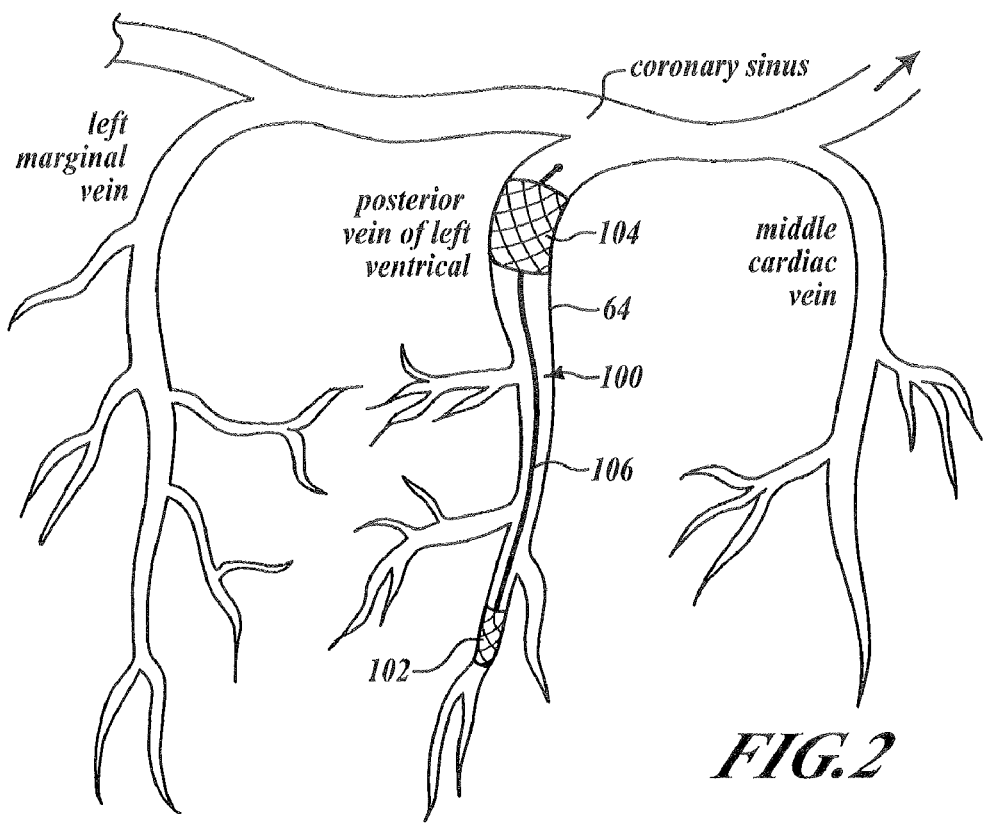
FIG. 2 illustrates one embodiment of a cardiac bridge deployed within a vein on the heart.

With reference now to FIG. 2, according to one embodiment of the present invention, a cardiac bridge 100 is deployed in a posterior vein 64 of the left ventricle. The cardiac bridge 100 includes a distal anchor 102, a proximal anchor 104 and an elongate bridge member 106 extending between the distal anchor 102 and the proximal anchor 104. As used herein, "distal" means the direction of a device as it is being inserted into a patient's body or a point of reference closer to the leading end of the device as it is inserted into a patient's body. Similarly, as used herein, "proximal" means the direction of a device as it is being removed from a patient's body or a point of reference closer to a trailing end of the device as it is being inserted into a patient's body. Preferably, the bridge member 106 is secured under tension between the distal anchor 102 and the proximal anchor 104 to provide a compressive force somewhat similar to that of a tightened seat belt. The inward compressive force along the length of the bridge member is exerted against the wall of the heart muscle for reducing the dilation of the ventricular wall. By reducing the dilation of the heart wall, the cardiac bridge effectively restores a more natural shape to the heart and thereby improves the cardiac efficiency of the heart.

Figure 3:
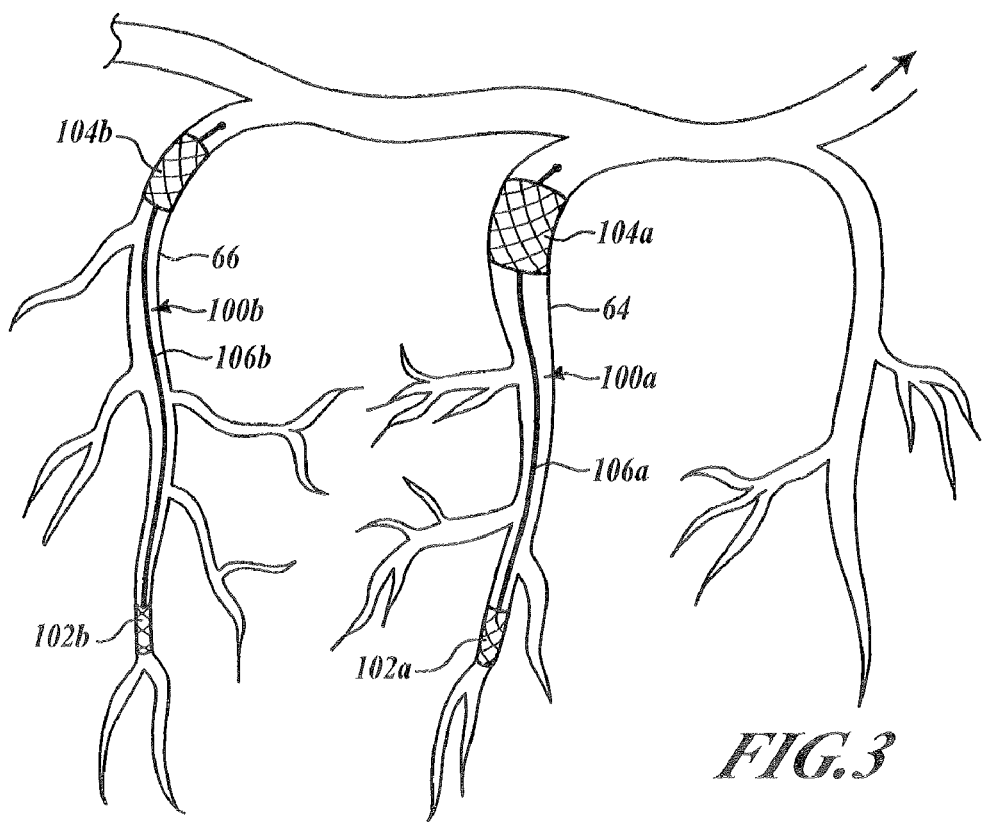
FIG. 3 illustrates a pair of cardiac bridges deployed within adjacent veins on the heart.

FIG. 3 illustrates an alternative embodiment wherein two cardiac bridges 100a and 100b are utilized to further reduce dilation of the heart wall. In particular, the cardiac bridges 100a and 100b are positioned in the posterior vein of the left ventricle 64 and the left marginal vein 66, respectively. Each cardiac bridge includes a distal anchor 102a, 102b, a proximal anchor 104a, 104b and a bridge member 106a, 106b disposed between the distal and proximal anchors. Each of the cardiac bridges 100a and 100b exerts a compressive force against a different area of the wall of the heart.

Figure 4:
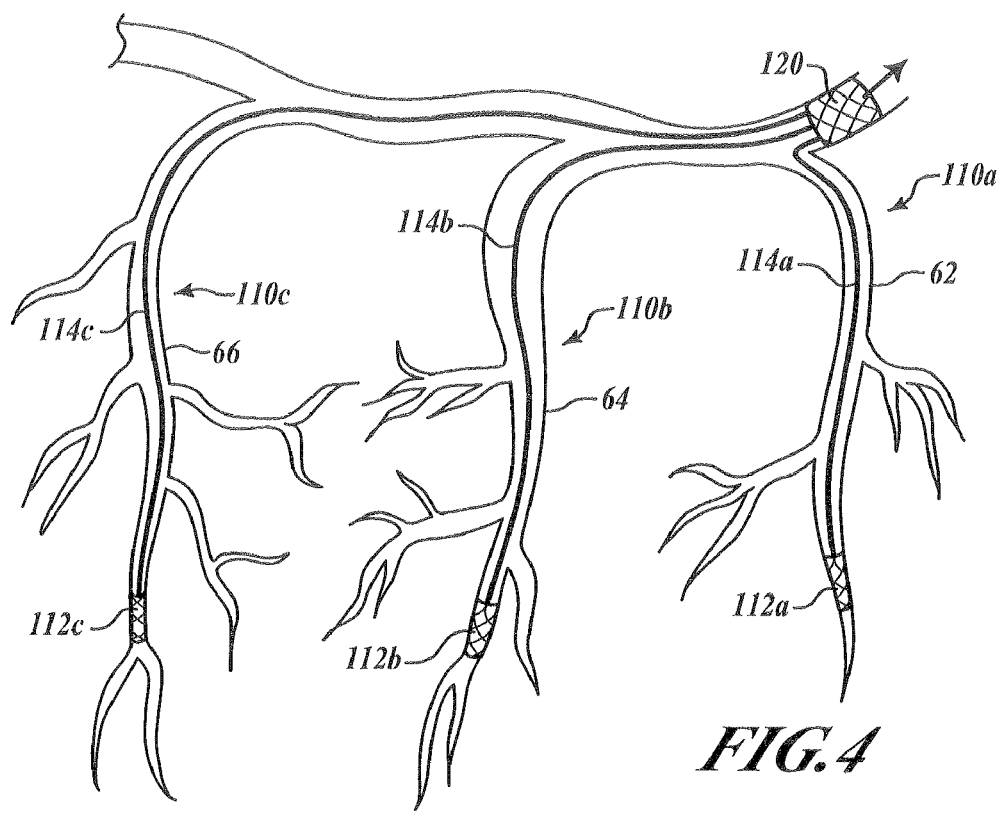
FIG. 4 illustrates three cardiac bridges positioned in veins on the heart wherein a proximal portion of each cardiac bridge is joined to a common anchor.

FIG. 4 illustrates another embodiment wherein three cardiac bridges 110a, 110b and 110c are positioned in the middle cardiac vein 62, the posterior vein of the left ventricle 64 and the left marginal vein 66, respectively. The cardiac bridge 110a includes a distal anchor 112a and a bridge member 114a. Similarly, the cardiac bridge 110b includes a distal anchor 112b and a bridge member 114b. Cardiac bridge 110c includes a distal anchor 112c and a bridge member 114c. In this configuration, the bridge members 114a, 114b and 114c are connected to a common proximal anchor 120. In one preferred arrangement, the proximal anchor 120 is located in the coronary sinus as shown. The bridge members 110a, 110b and 110c may be selectively tightened between the distal anchors and the proximal anchor 120 as necessary to exert an inward force against the wall of the heart to reduce ventricular dilation. It will be appreciated that, by providing multiple bridges which extend along different planes and can be independently adjusted, the physician is provided with the ability to manipulate the geometry of the heart in a substantially three dimensional manner.

Figure 5:
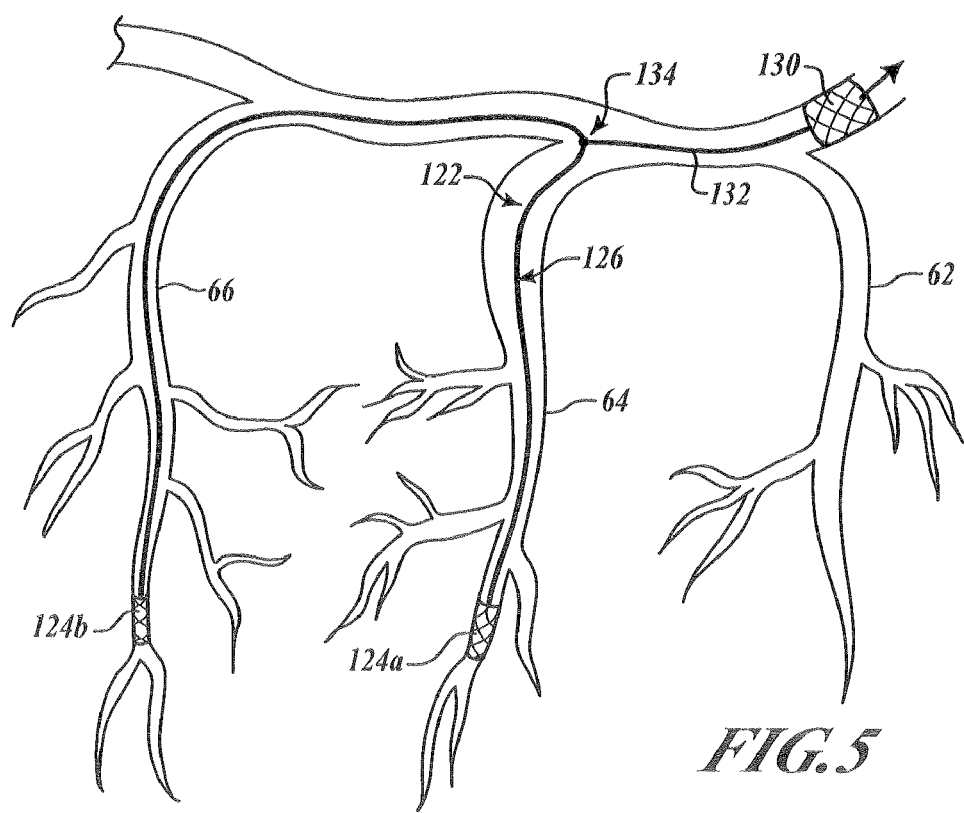
FIG. 5 illustrates a pair of cardiac bridge members joined to a common proximal anchor within a vessel on the heart.

FIG. 5 illustrates another embodiment of a cardiac bridge 122 that includes a pair of distal anchors 124a, 124b having a common bridge member 126 extending therebetween. The distal anchor 124a is located in a first vessel, such as the posterior vein of the left ventricle 64 and the second distal anchor 124b is located in a second vessel, such as the left marginal vein 66. The bridge member 126 is secured to a proximal anchor 130 that is located in another vessel such as, for example, the coronary sinus. In the illustrated embodiment, the bridge member 126 is connected to the proximal anchor 130 via a tether 132. In one embodiment, a proximal end of the tether 132 is secured to the proximal anchor 130 and a distal end of the tether 132 is connected to the bridge member 126, preferably with a loop 134 or other slidable coupling member, thereby allowing the tether 132 to move along the bridge member 126. Alternatively, the distal end of the tether 132 may be fixedly secured to the bridge member 126.

Figure 6:
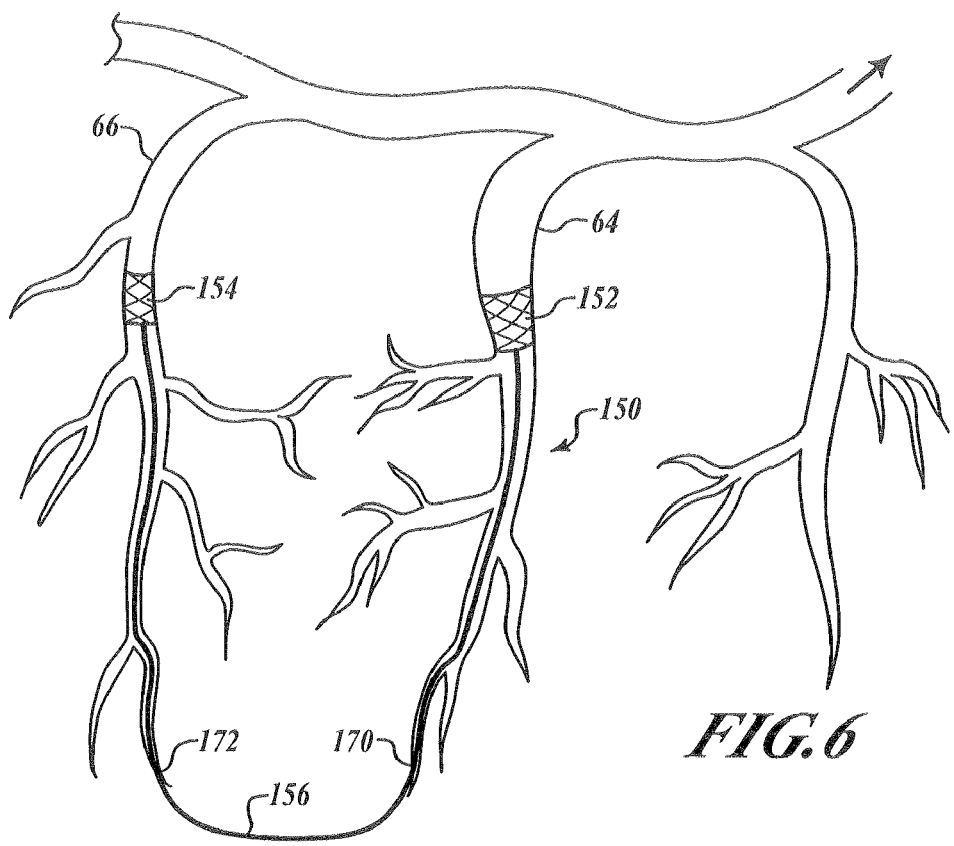
FIG. 6 illustrates a pair of anchors positioned in adjacent vessels on the heart and a bridge member extending between the anchors.

FIG. 6 illustrates yet another embodiment of a cardiac bridge 150 that includes a pair of anchors 152, 154. Each of the anchors 152, 154 is located in a different vessel and a bridge member 156 extends therebetween. The anchor 152 is located in a first vessel such as the posterior vein of the left ventricle 64 while the second anchor 154 is located in a second vessel such as the left marginal vein 66. The bridge member 156 preferably extends distally from the anchor 152 within the vessel toward the apex of the heart. In preferred configurations, the bridge member 156 extends inside connecting veins (also called collaterals, not shown) between adjacent vessels, such as a posterior vein of the left ventricle 64 and a left marginal vein 66. In locations or anatomies wherein it is not possible to connect via collateral vessels, the bridge member 156 may also perforate the vessel at a location 170, extend across the exterior of the heart and enter the second vessel at a location 172 in the area towards the apex. The bridge member 156 is passed through the vessel in a direction towards the coronary sinus where it is secured to the second anchor 154. In one embodiment, an end of the bridge member 156 can be selectively tightened to one or both of the anchors 152, 154 to apply sufficient inward force to the ventricle wall to reduce cardiac dilation.

Figure 7:
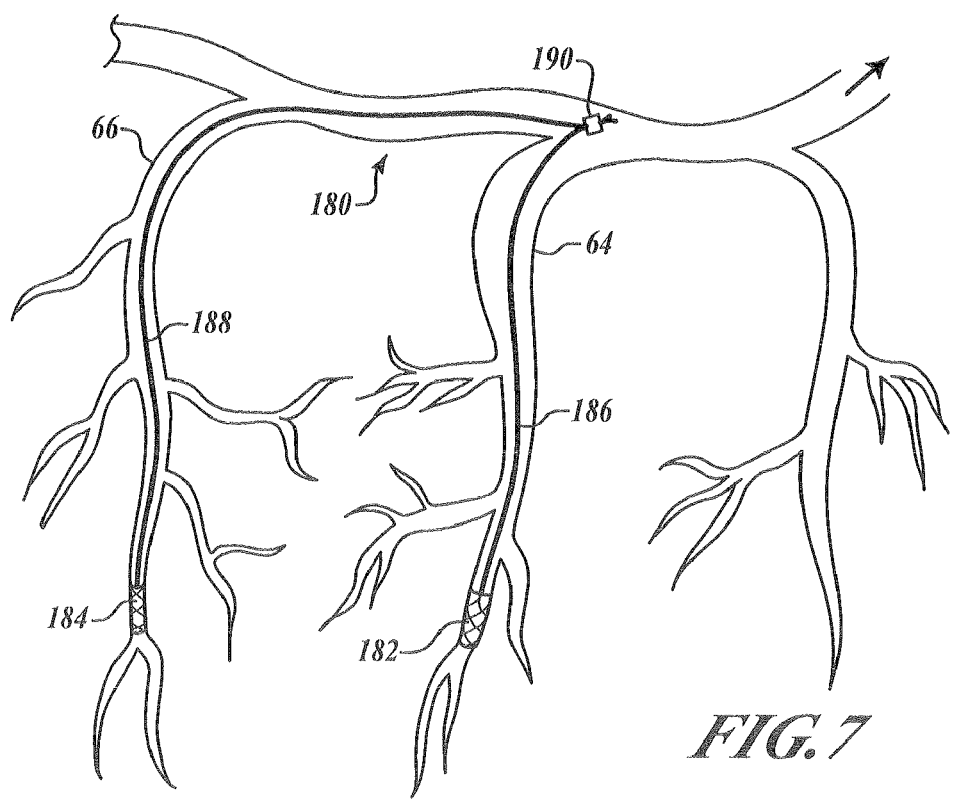
FIG. 7 illustrates a pair of bridge members secured together at one end with a coupling member.

FIG. 7 illustrates yet another embodiment of a cardiac bridge 180 that includes a first anchor 182 that is positioned in a first vessel such as the posterior vein of the left ventricle 64 and a second anchor 184 that is positioned in another vessel such as the left marginal vein 66. A first bridge member 186 is connected at one end to the first anchor 182 and a second bridge member 188 is connected at one end to the second anchor 184. The proximal ends of the bridge members 186 and 188 are joined by an attachment mechanism 190, such as a clip or other suitable fastener. The attachment mechanism may include a fixed or a movable connection allowing the bridge members 186, 188 to be selectively tightened as necessary to apply sufficient inward force to the wall of the heart muscle to reduce cardiac dilation. In one alternative configuration, the bridge members 186, 188 may be simply twisted or otherwise secured together to form the anchor.

Figure 8:
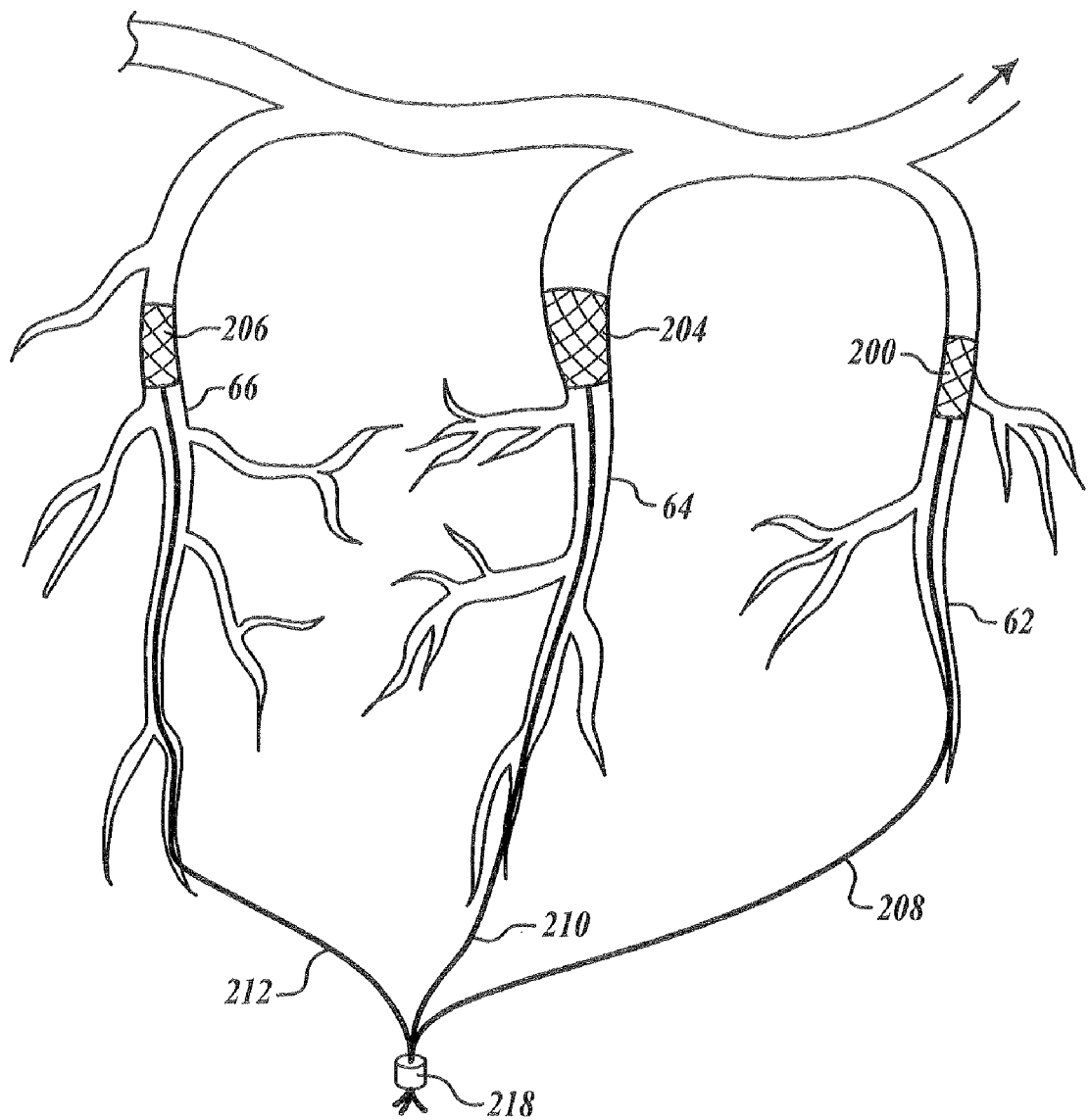
FIG. 8 illustrates a number of cardiac bridges including two or more anchors positioned in different vessels and bridge members that are commonly joined at one end at a location on the exterior of the heart.

FIG. 8 illustrates yet another configuration wherein cardiac bridges have anchors positioned in two or more vessels. In the configuration shown, there are three anchors 200, 204 and 206 which are positioned in different vessels of the heart. A bridge member 208 has one end secured to the anchor 200. A second bridge member 210 has one end secured to the anchor 204. A third bridge member 212 is secured to the anchor 206. The bridge members 208, 210 and 212 extend through their respective vessels towards the apex of the heart. In certain configurations, the bridge members perforate the vessel walls in the area of the apex and are joined to a coupling member 218 located on the exterior of the heart muscle. In other configurations, the bridge members may be joined within the vessels.

In one embodiment, the coupling member 218 includes one or more locking mechanisms that allow the bridge members 208, 210 or 212 to be selectively tightened as necessary to apply a sufficient inward force to the walls of the heart to reduce ventricular dilation. In one preferred configuration, the coupling member takes the form of a slideable clip. The clip may be advanced over the bridge members in an open condition and then adjusted to a closed condition to couple the ends of the bridge members together. In one construction, the clip may be formed of a shape memory material which is biased toward the closed condition. Alternatively, the bridge members could be configured to be attached without the use of a coupling member. For example, the bridge members could be twisted or tied together.

Figure 9A:
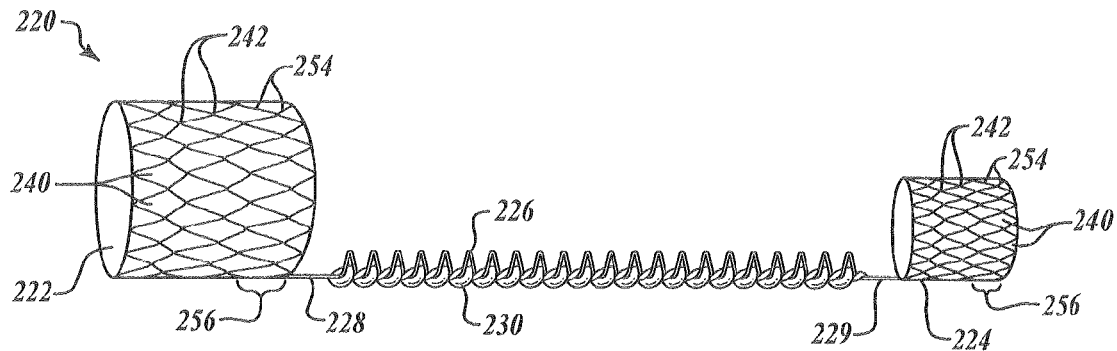
FIG. 9A illustrates one embodiment of a cardiac bridge including a proximal and distal anchor and an elongate bridge member extending therebetween.
Figure 9B:
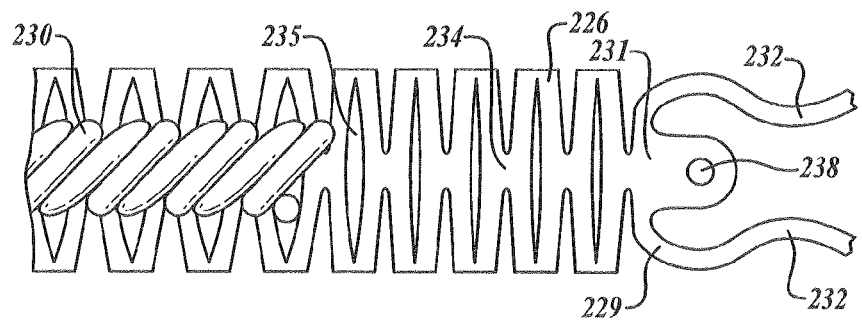
FIG. 9B illustrates one embodiment of a bridge member.

FIGS. 9A and 9B illustrate one embodiment of a cardiac bridge 220 which includes a resorbable material 230. The cardiac bridge is an adaptation of a medical device described in U.S. Published Patent Application Number 2007/0073391 A1 published Mar. 29, 2007, which is herein incorporated by reference in its entirety.

The cardiac bridge 220 includes a proximal anchor 222 and a distal anchor 224 that are joined by a bridge member 226. In one embodiment, the bridge member 226 is constructed with a shape-memory material or a spring-like structure that gradually foreshortens to increase the tension between the proximal and distal anchors after the cardiac bridge has been implanted. The bridge member is selected to have a length and stiffness such that it can exert sufficient force on the heart wall to reduce ventricular dilation as desired. In the illustrated embodiment, the resorbable material 230 is disposed between individual links of the bridge member 226. The resorbable material 230 holds the links of the bridge member 226 in an elongated state during delivery and deployment. However, over time, the material 230 is reabsorbed thereby allowing the links to collapse such that the bridge member is allowed to shorten.

Resorbable materials are those that, when implanted into a human body, are absorbed by the body by means of an enzymatic degradation, hydrolysis and/or by active absorption by blood cells and tissue cells in the human body. Examples of resorbable materials are PDS (Polydioxanone) Pronova (Poly-hexafluoropropylen-DDF), Maxon (Polyglyconat), Dexon (polyglycolic acid) and Vicryl (Polyglactin). As explained in more detail below, a resorbable material may be used in combination with a shape memory material such as Nitinol, Elgiloy or spring steel to allow the super elastic material to return to a predetermined shape over a period of time.

In one embodiment as shown in FIG. 9A, the proximal and distal anchors 222, 224 are both made like cardiac stents, i.e., generally cylindrical tubes made of shape memory material, such as for example, Nitinol. However, the anchors 222, 224 may also be made of any other suitable material such as stainless steel. In the illustrated embodiment, both anchors 222, 224 have a mesh configuration comprising loops 254 of zigzag shaped shape memory material having alternating peaks 242. The loops 254 are connected at each peak 242 to form rings 256 of four sided openings 240. Although one particular type of anchor mechanism is shown for purposes of illustration, it will be appreciated that a wide variety of anchoring mechanisms may be used.

The proximal and distal anchors 222, 224 each have a compressed state and an expanded state. In a compressed state, the anchors 222, 224 have a diameter that is less than the diameter of the vessel in which the cardiac bridge is to be deployed. In a compressed state, the anchors 222, 224 preferably have a substantially uniform diameter of about between 1.5 mm and 4 mm. In the expanded state, the proximal and distal anchors 222, 224 have a diameter that is preferably about equal or slightly greater than the inner diameter of the section of the vessel in which the anchor will be deployed.

In the embodiment shown, the bridge member 226 is connected between the proximal anchor 222 and the distal anchor 224 by links 228, 229. More specifically as shown in FIG. 9B, proximal link 228 connects the proximal anchor 222 to the proximal end of the bridge member 226 and the distal link 229 connects the distal anchor 224 to the distal end of the bridge member 226. The links 228 and 229 have a base 231 and arms 232 that extend from the base and that are connected to peaks 242 on each anchor 222, 224. Further, the links 228, 229 may be provided with a hole 238 as shown in FIG. 9B, which serves as a means through which the end of a resorbable thread may be secured to the bridge member 226.

In one embodiment, the bridge member 226 is made from a shape memory material and is sufficiently flexible to allow the cardiac bridge 220 to conform to the shape of the vessel surrounding the dilated ventricle. The bridge member 226 comprises X-shaped elements 234, wherein each X-shaped element is connected to an adjacent X-shaped element at the extremities of the X, allowing a space 235 to be created between adjacent X-shaped elements as shown in FIG. 9B. The X-shaped elements 234 further have rounded edges that minimize the chance that a sharp edge of the bridge member 226 will puncture or cut a part of the vessel during delivery.

Bridge member 226 has two states: an elongated state in which the bridge member has a first length, and a shortened stated in which the bridge member has a second length. The second length is shorter than the first length. As discussed above, a resorbable material such as a resorbable thread 230 is woven into the spaces 235 (shown schematically in FIGS. 9A and 9B) between adjacent X-shaped elements 234 of the bridge 226 in its elongated state. The thread 230 acts as a temporary spacer. When a resorbable thread 230 is dissolved over time, the bridge member gradually contracts. As the bridge member contracts, the bridge member adjusts from a curved shape toward a straighter shape. This adjustment creates a compressive force along the heart wall for treating ventricular dilation.

Figure 10:
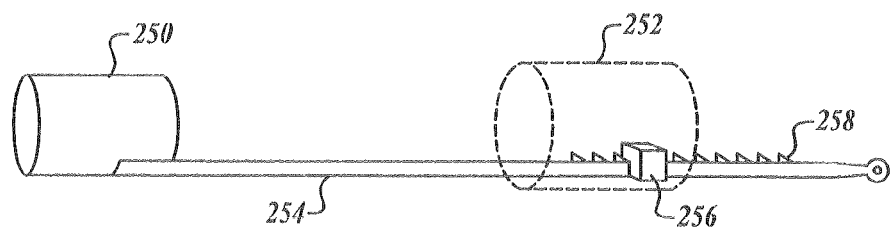
FIG. 10 illustrates another embodiment of a cardiac bridge including a locking mechanism within an anchor.

FIG. 10 illustrates an embodiment of a cardiac bridge including a first anchor 250 and a second anchor 252 with a bridge member 254 disposed therebetween. The bridge member 254 is secured to the first anchor 250 by a fixed connection and is secured to the second anchor 252 with a movable locking mechanism 256 such as a ratchet. In one embodiment, the bridge member 254 is formed as a wire that includes a number of serrations 258 or other features along all or a portion of its length that pass through a pawl within the locking mechanism 256 in a manner similar to a plastic zip tie. The bridge member 254 may be secured to the distal anchor 250 with a weld, an adhesive or a knot. The tension between the anchors 250, 252 can be increased by pulling the bridge member 254 through the locking mechanism to tension the cardiac bridge on the heart muscle. However, the serrations or other features cannot move backwards through the locking mechanism such that the tension between the anchors 250, 252 cannot relax. Other examples of locking mechanisms for use in a medical device can be found in US Patent Publication No. 2006/0276890A1 published Dec. 7, 2006, which is herein incorporated by reference.

FIG. 11A illustrates one example of a delivery mechanism for inserting a cardiac bridge into a vessel surrounding a dilated ventricle. In one embodiment, the delivery mechanism 300 includes an inner sheath 302 and an outer sheath 308 that extends over the inner sheath. A cardiac bridge 310 includes a distal anchor 312, proximal anchor 314, and a bridge member 316 that extends between the proximal anchor and distal anchor. In one embodiment, the distal anchor 312 and proximal anchor 314 are formed like self-expanding stents that are compressed against the outer surface of the inner sheath 302. The inner sheath 302 may include one or more marker bands 320 made from a material that is visible under fluoroscopy or other medical imaging technique to allow the physician to determine where the inner sheath and cardiac bridge are placed in the body. A pusher sheath 322 is positioned over the inner sheath 203 proximal to the cardiac bridge 310. The pusher sheath 322 has a diameter to allow it to fit over the inner sheath 302 and within the inner diameter of outer sheath 308. The pusher sheath 322 helps prevent the cardiac bridge 310 from moving proximally on the inner sheath 302 during insertion of the inner sheath into the body. The inner sheath 302 preferably includes one or more lumens that accommodate a guide wire 326. The guide wire 326 is advanced into the body such that the inner sheath 302 can be tracked over the guide wire 326 to position the cardiac bridge 310 at a desired location. The distal anchor 312 is deployed at the desired location in a cardiac vessel by withdrawing the outer sheath 308 proximally to uncover the distal anchor 312. The self-expanding nature of the stent used to form the distal anchor 312 allows it to expand radially in the vessel and seat against the interior of the vessel wall.

With the distal anchor freed from the inner sheath 302, the inner sheath can be withdrawn proximally thereby tensioning the bridge member 316. The outer sheath 308 can be further withdrawn to uncover the proximal anchor 314 thereby allowing it to radially expand against the interior of the vessel wall. In one embodiment, resorbable materials within the bridge member 316 begin to dissolve once the bridge is placed in the vessel, thereby allowing the bridge member to exert further force against the anchors 312, 314 and against the wall of the ventricle. A further description of the deployment mechanism, including a handle for moving the outer sheath 308 with respect to the inner sheath 302, is found in the US Published Patent Application 2007/00773391A1 mentioned above.

In one embodiment, a delivery mechanism 300 is used to place one or more cardiac bridges in vessels surrounding the dilated ventricle in a manner shown in FIGS. 2 and 3. In one procedure, an incision is made into a patient's blood vessel such as the femoral vein or a jugular vein and an introducer sheath is placed in the incision. A guide wire is inserted into the introducer sheath and advanced to the right atrium of the heart, through the coronary ostium and into the coronary sinus. From the coronary sinus, the guide wire is further advanced into a vessel extending along the exterior of the dilated ventricle. Upon placement of the guide wire, a guide catheter and dilator can be advanced over the guide wire and into the coronary vessel where the cardiac bridge is to be placed. The dialator can then be withdrawn and the delivery mechanism 300 advanced through the guide catheter to a desired location whereupon the guide catheter can be withdrawn from the patient. The cardiac bridge is then deployed in the manner described above.

FIG. 11B illustrates one embodiment of a delivery mechanism 350 that may be used to deploy a cardiac bridge having anchors located in different vessels such as the configuration shown in FIG. 5. In this embodiment, a delivery mechanism 350 includes an outer sheath 352 and two or more inner sheaths 354, 356. Each of the inner sheaths supports a distal anchor and has a lumen through which a guide wire can be routed. An anchor 358 is positioned on the outer surface of the sheath 354 and an anchor 360 is positioned on the outer surface of the sheath 356. In one embodiment, each of the anchors is a self-expanding stent. However, it is possible to use balloon expandable stents. Each of the sheaths 354, 356 has an outer cover (not shown) that is retractable to deploy the anchors 358, 360. The anchors 358, 360 are joined by a cardiac bridge member 362 having one end secured to each of the anchors 358 and 360.

A proximal anchor 380 is positioned on the outer sheath 352. The proximal anchor 380 is joined to the bridge member 362 via a tether 382. An outer cover (not shown) over the proximal anchor allows the proximal anchor 380 to expand when removed. The tether 382 is coupled to the bridge member 362 with a slidable or fixed connection at the point where it joins the bridge member 362.

In use, the delivery mechanism 350 is placed near the location in the vessels where the cardiac bridge is to be deployed. The guide wires are positioned in the vessels where the distal anchors are to be placed and the sheaths 354, 356 are routed over the guide wires. Covers over the sheaths 354, 356 are withdrawn to allow the anchors 358, 360 to expand. The outer sheath 352 can then be withdrawn proximally to tension the bridge member 362 before deploying the proximal anchor 380.

Figure 11C:
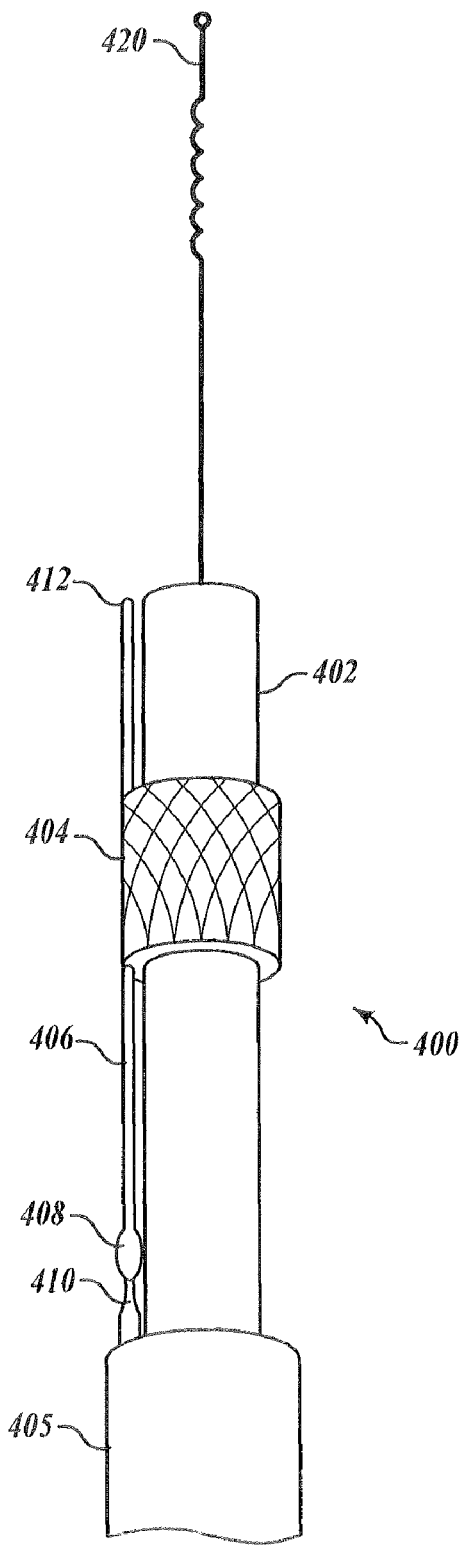
FIG. 11C illustrates another embodiment of a delivery device for placing a cardiac bridge into a heart vessel.

FIG. 11C illustrates another embodiment of a delivery mechanism 400 comprising an inner sheath 402 and an outer sheath 405 that is retractable over the inner sheath. An anchor 404 is positioned on the inner sheath and is either self-expanding when the outer sheath 405 uncovers the anchor 404 or may be expandable with a balloon. A bridge member 406 is slidably secured to the anchor 404 with a hypotube, or the like, that is bonded to the anchor. In one embodiment, the bridge member 406 has an enlarged proximal end that engages the hypotube so that it cannot be pulled through the anchor. A breakable link 410 in the bridge member allows the bridge member to be broken at a desired location during deployment. A distal end 412 of the bridge member 406 may be pointed to allow it to perforate a vessel during deployment.

During use, the inner sheath 402 is advanced over a guide wire 420 into a vessel. The anchor 404 is deployed and the bridge member 406 is advanced distally into the end of a vessel where is perforates the vessel as shown in FIGS. 6 and 8. Once outside the vessel, a surgeon can secure a distal end of the bridge member to a common anchor 218 as shown in FIG. 8 or can route the distal end back into a vessel for fastening to another anchor as shown in FIG. 6. Once the distal end is secured, the breakable link 410 can be broken and the proximal section withdrawn from the patient.

The delivery mechanism 400 can also be used to deploy the cardiac bridge configuration shown in FIGS. 4 and 7. In that embodiment, the bridge member is reversed on the inner catheter so that a proximal end extends outside the patient and the distal end is enlarged to engage the anchor 404.

In the configuration shown in FIGS. 4 and 7, cardiac bridges have distal anchors and bridge members secured thereto. In this embodiment, the bridge members have a length that allows a proximal end to remain outside the body as it is being deployed. A common anchor 120, 190 is threaded over the free proximal ends of the bridge members with a catheter. The catheter may include a tool for cutting the bridge members to the appropriate length. Alternatively, the bridge members may have a breakable portion that allows the excess length to be removed from the patient.

Figure 12A:
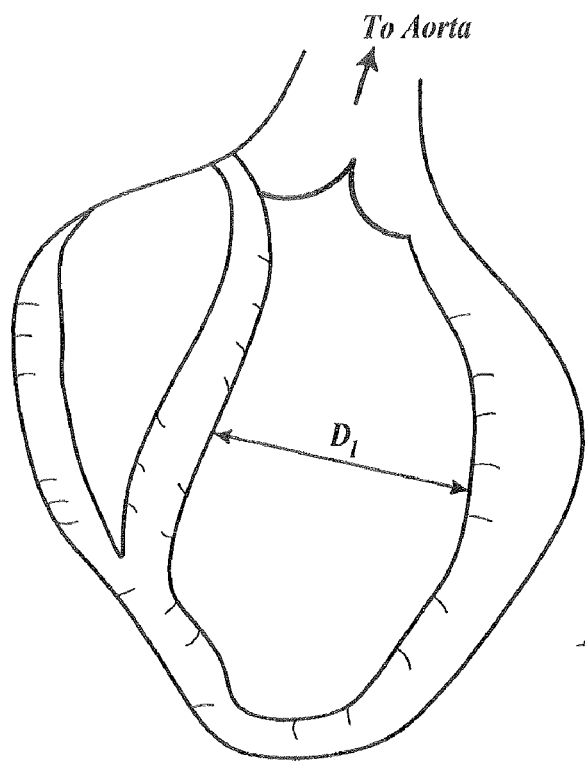
FIG. 12A is a cross-sectional view of a heart having an enlarged left ventricle.
Figure 12B:
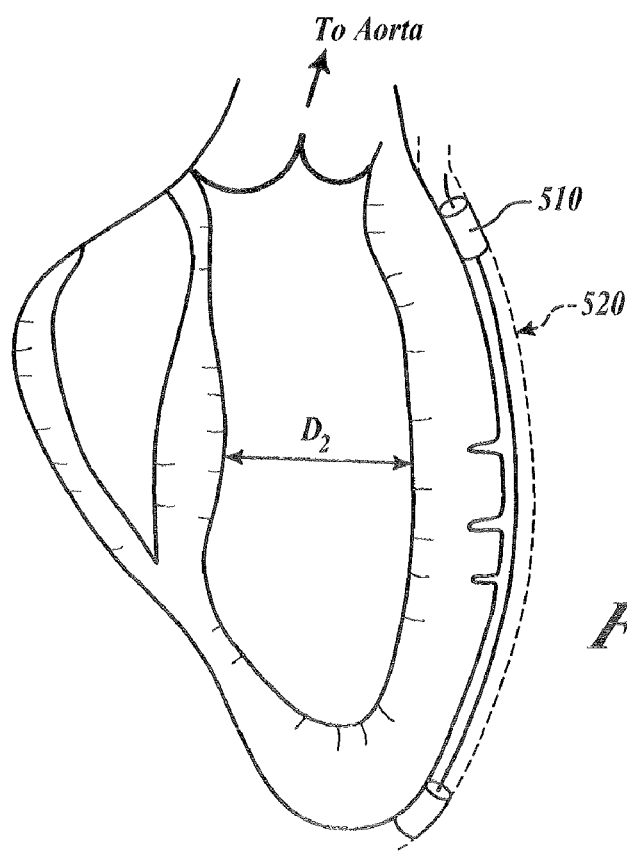
FIG. 12B is a cross-sectional view of the heart of FIG. 12A with a cardiac bridge secured within a vessel for applying a compressive force along the enlarged region.

With reference now to FIG. 12A, a cross-sectional view of a dilated heart 50 is provided. The distance $D_1$ or diameter of the left ventricle is larger than would be expected for a healthy heart. FIG. 12B illustrates the heart 50 after placement of a cardiac bridge 510 in a vessel 520 surrounding the dilated ventricle. The cardiac bridge 510 is tensioned to produce a new diameter $D_2$ of the left ventricle that is smaller than the diameter $D_1$ and restores the heart to a more normal shape.

Figure 12C:
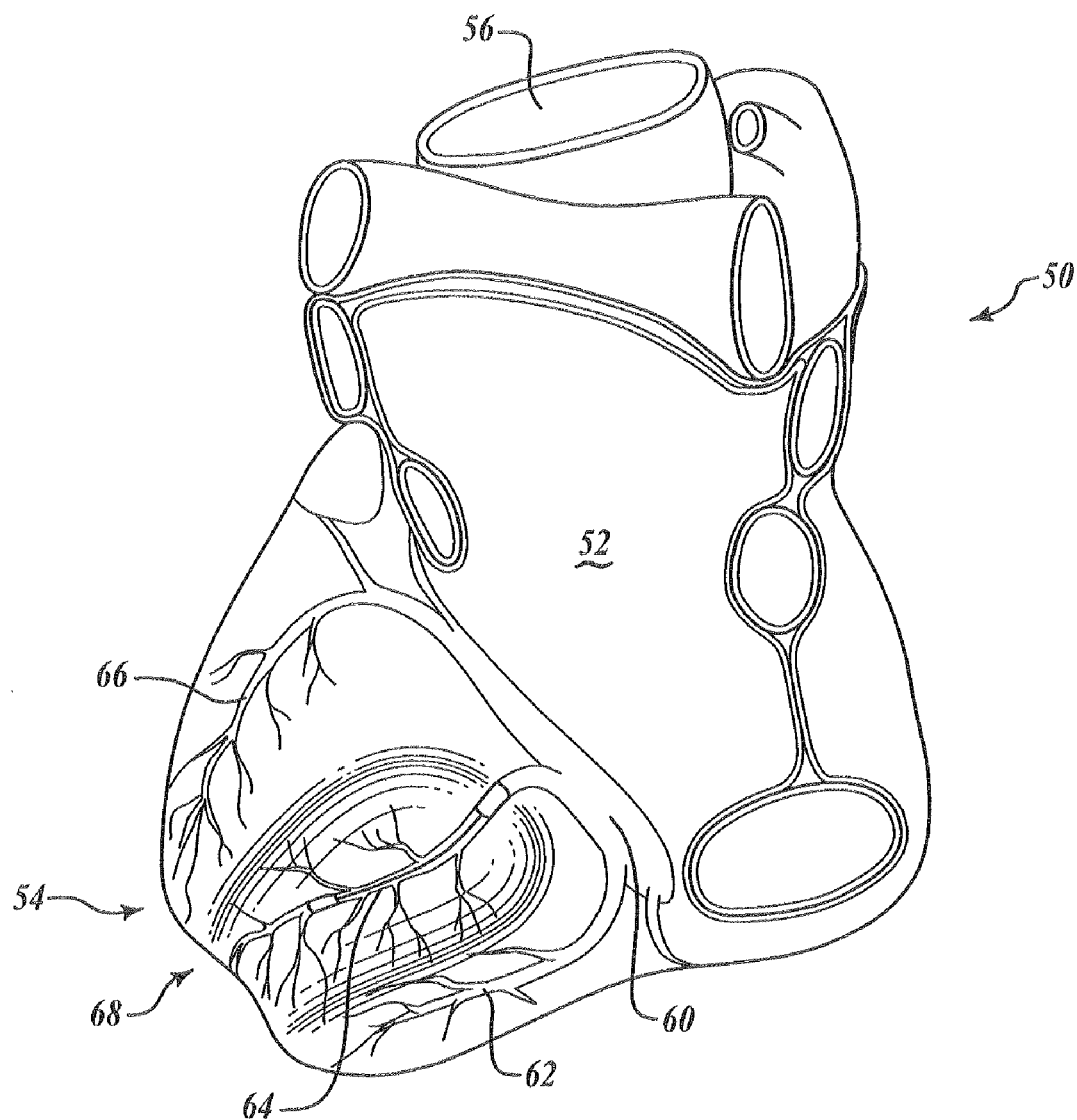
FIG. 12C is a posterior view of the heart of FIG. 12A with a cardiac bridge positioned in a vessel for reducing ventricular dilation.

FIG. 12C illustrates a posterior view of the heart with a cardiac bridge positioned in the posterior vein of the left ventricle. As depicted, the cardiac bridge reduces the ventricular dilation of the heart muscle and restores the heart to a more normal shape.

Figure 13A:
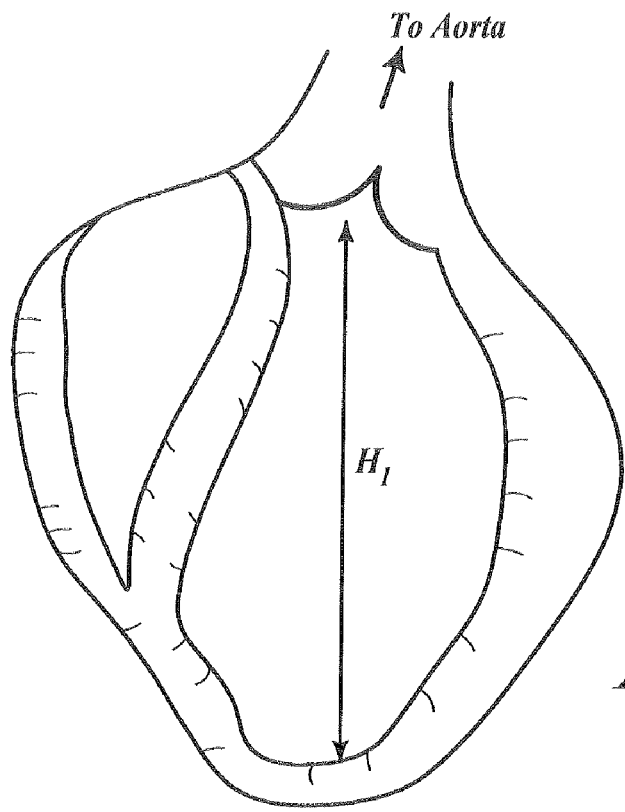
FIGS. 13A through 13D illustrate changes in the dimensions of the heart resulting from a treatment method according to preferred embodiments of the present invention.
Figure 13B:
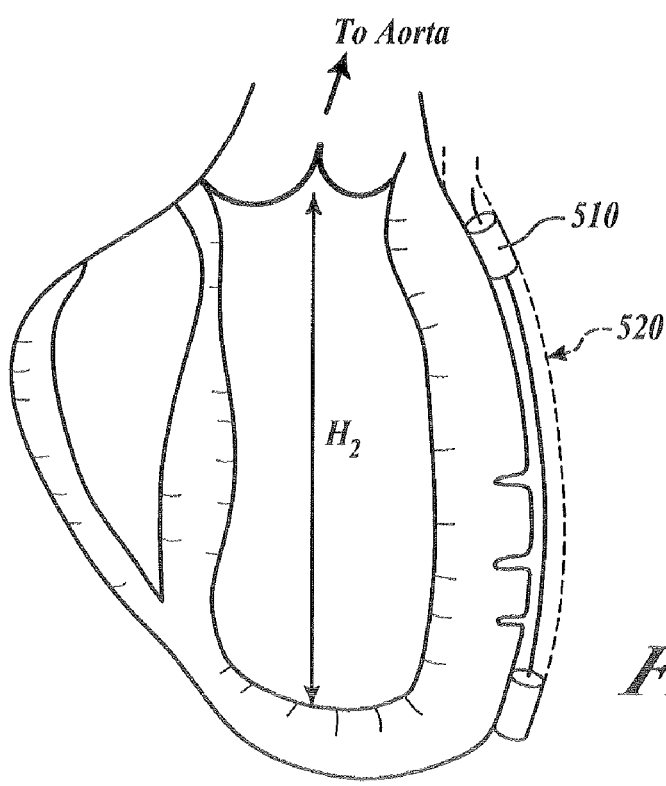
Figure 13C:
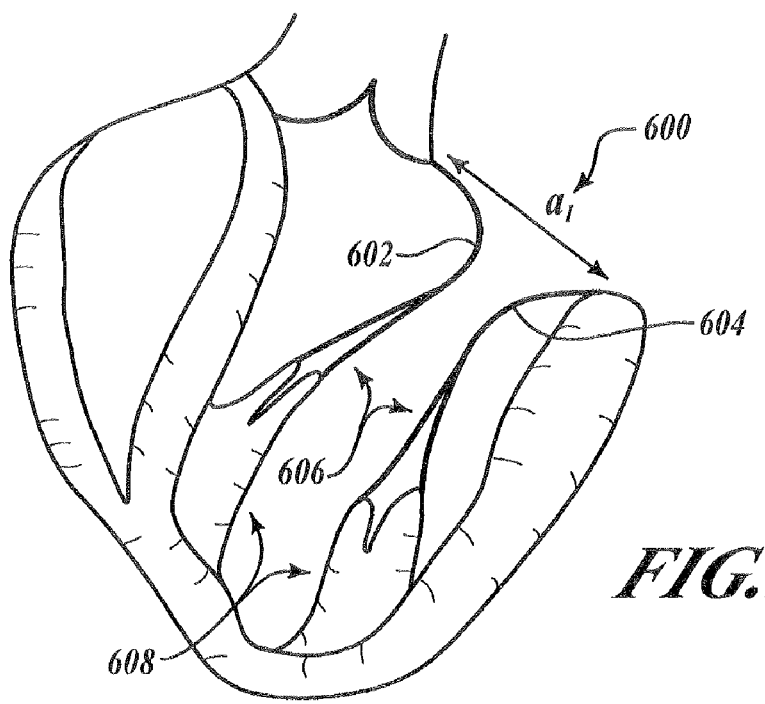

FIGS. 13A through 13D illustrate how the disclosed technology may be used to improve the operation of a heart valve. As shown in FIG. 13A, the height $H_1$ of a heart with a dilated ventricle may be greater than that of a healthy heart. In this condition, there is excessive tension in the chordae tendinae which prevents the mitral valve leaflets from closing properly. With one or more cardiac bridges 510 installed in a vessel(s) 520 of the heart, the height may be reduced to lesser value $H_2$ as shown in FIG. 13B. The reduction in height improves the functioning of mitral valve by reducing tension on the chordae tendinae. With reference now to FIG. 13C, the mitral valve 600 is illustrated for purposes of additional explanation regarding how the present invention may be used to improve valve function. The mitral valve has an anterior leaflet 602 and a posterior leaflet 604 that open and close to control blood flow through the valve. As discussed above, each leaflet is attached by chordae tendinae 606 to papillary muscles 608 within the interior of the ventricle. The chordae tendinae prevent the mitral valve leaflets 602, 604 from prolapsing upward into the left atrium.

Figure 13D:
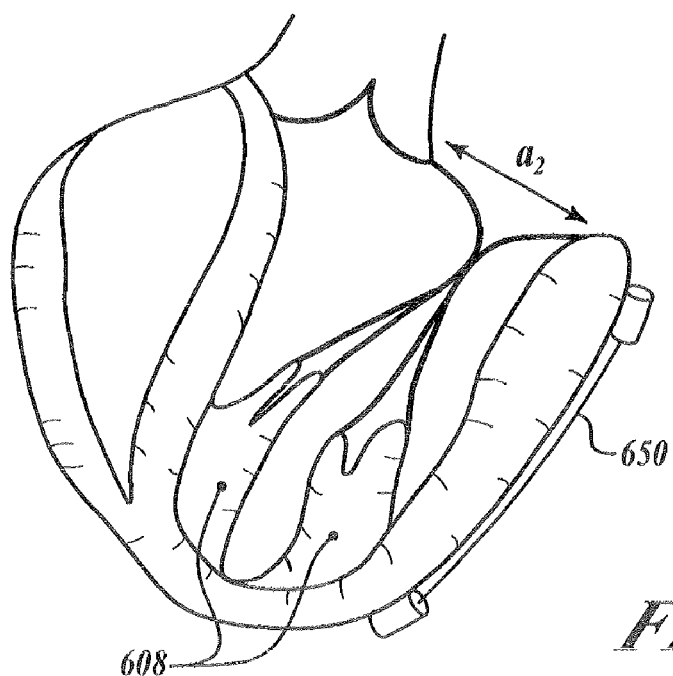

When a heart becomes dilated, the papillary muscles 608 are often laterally dislocated compared with each other and the diameter of the mitral valve $a_1$ increases compared with a healthy heart. The dislocated papillary muscles create extra tension in the chordae tendinae, which prevents the leaflets from closing completely. By adding one or more cardiac bridges 650 into vessels of the heart as shown in FIG. 13D, the heart muscle is reshaped and the papillary muscles 608 are moved closer together. As a result, the extra tension on the chordae tendinae is eliminated such that the diameter of the mitral valve a2 is reduced and the mitral valve functions properly.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope of these claims and equivalents thereof.

We claim:

1. A method of reducing left ventricular dilation, comprising:
   advancing at least a portion of a cardiac bridge into a posterior vein of a left ventricle, the cardiac bridge including a proximal anchor, a distal anchor and a bridge member connecting the proximal and distal anchors;
   expanding the proximal and distal anchors; and
   altering a curvature of the bridge member between the proximal and distal anchors such that the bridge member applies a compressive force to a wall of the left ventricle.

2. The method of claim 1, wherein the curvature of the bridge member is altered by increasing tension in the bridge member, thereby causing the bridge member to adjust toward a straighter configuration.

3. The method of claim 2, wherein a resorbable material is provided along the bridge member for maintaining the bridge member in an elongated configuration and wherein the resorbable material is resorbed over time for gradually reducing a length of the bridge member.

4. The method of claim 1, wherein the cardiac bridge is formed at least in part of a shape memory material.

5. The method of claim 1, wherein the proximal and distal anchors comprise expandable stents.

6. A method of reducing ventricular dilation, comprising:
advancing at least a portion of a first cardiac bridge into a first vein that branches from a coronary sinus and extends along a length of a left ventricle, the first cardiac bridge including a first proximal anchor, a first distal anchor and a first bridge member;
advancing at least a portion of a second cardiac bridge into a second vein that branches from the coronary sinus and extends along the length of the left ventricle, the second cardiac bridge including a second proximal anchor, a second distal anchor and a second bridge member;
joining the first and second bridge members; and
increasing tension in the first and second bridge members such that the bridge members applies a compressive force to the ventricular wall.

7. The method of claim 6, wherein joining the first and second bridge members comprises securing ends of the first and second bridge members with a coupling member at a location proximal to the first and second proximal anchors.

8. The method of claim 7, wherein the coupling member is an advanceable clip which is configured to slide over the first and second bridge members and has an open configuration for advancement and a closed configuration for securing the bridge members.

9. The method of claim 7, further comprising removing a portion of the first and second bridge members proximal to the coupling member.

10. The method of claim 6, wherein joining the first and second bridge members comprises securing ends of the first and second bridge members with a coupling member at a location distal to the first and second distal anchors.

11. The method of claim 10, wherein the first and second bridge members are secured to the coupling member in a region along an apex of the heart.

12. The method of claim 6, wherein joining the first and second bridge members comprises securing ends of the first and second bridge members to an anchoring member deployed in the coronary sinus.

13. A method for improving coaption of leaflets of a mitral valve, comprising:
advancing at least a portion of a cardiac bridge into a posterior vein of the left ventricle, the cardiac bridge including a proximal anchor, a distal anchor and a bridge member connecting the proximal and distal anchors;
expanding the proximal and distal anchors; and
applying tension to the bridge member for reducing a height of a left ventricle and thereby reducing tension on the chordae tendinae.

* * * * *